//‍

United States Patent [19]

White et al.

[11] 3,996,207

[45] Dec. 7, 1976

[54] DERIVATIVES OF TETRAHYDRO-1H-1,3-DIAZEPINE AND HEXAHYDRO-1,3-DIAZOCINE

[75] Inventors: Alan Chapman White, Windsor; Robin Michael Black, Porton, both of England

[73] Assignee: John Wyeth & Brother Limited, Maidenhead, England

[22] Filed: May 29, 1975

[21] Appl. No.: 582,038

Related U.S. Application Data

[63] Continuation-in-part of Ser. No. 472,759, May 23, 1974, Pat. No. 3,926,994, which is a continuation-in-part of Ser. No. 309,580, Nov. 24, 1972, abandoned.

[30] Foreign Application Priority Data

Dec. 14, 1971  United Kingdom ............... 1250/71
Mar. 15, 1972  United Kingdom ............. 12069/72
Nov. 30, 1972  United Kingdom ............. 11199/72
May 31, 1973  United Kingdom ............. 26079/73

[52] U.S. Cl. .......................... 260/239 BC; 424/244
[51] Int. Cl.² ............. C07D 243/04; C07D 245/02
[58] Field of Search ............................. 260/239 BC

[56] References Cited
UNITED STATES PATENTS 3,657,229  4/1972  Bailey .......................... 260/239 BC

*Primary Examiner*—Nicholas S. Rizzo
*Assistant Examiner*—D. B. Springer

[57] ABSTRACT

The disclosure relates to derivatives of tetrahydro-1H-1,3-diazepine and hexahydro-1,3-diazocine of the general formula

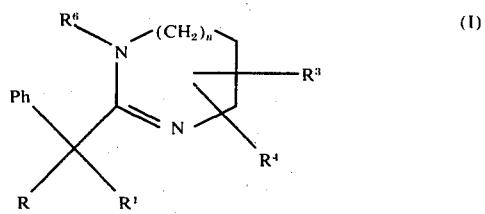

or pharmaceutically acceptable acid addition salts thereof wherein n represents 2 or 3, $R^3$ and $R^4$ which may be the same or different each represent hydrogen or lower alkyl, Ph represents phenyl, halophenyl, lower alkyl phenyl, di(lower alkyl) phenyl or lower alkoxy phenyl, R is hydroxyl, lower alkoxy or halogen, $R^1$ is phenyl, halophenyl, lower alkyl phenyl, di(lower-alkyl) phenyl, lower alkoxyphenyl or naphthyl and $R^6$ is hydrogen or lower alkyl. The compounds have hypoglycemic activity.

5 Claims, No Drawings

DERIVATIVES OF TETRAHYDRO-1H-1,3-DIAZEPINE AND HEXAHYDRO-1,3-DIAZOCINE

This application is a continuation-in-part of co-pending United States Patent Application Ser. No. 472,759 filed May 23, 1974 entitled "Heterocyclic Compounds" (now U.S. Pat. No. 3,926,994, granted Dec. 16, 1975) which in turn is a continuation-in-part of United States Patent Application Ser. No. 309,580 filed Nov. 24, 1972 entitled "Heterocyclic Compounds," now abandoned. This invention relates to heterocyclic compounds and more particularly to derivatives of tetrahydro-1H-1,3-diazepine and hexahydro-1,3-diazocine, to processes for preparing these compounds and to pharmaceutical preparations containing them.

The compounds of the present invention are those of general formula

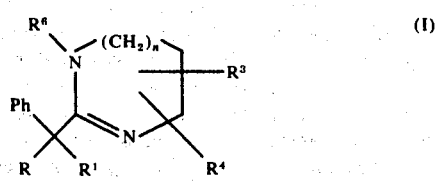

and their pharmaceutically acceptable acid addition salts, wherein n represents 2 or 3, $R^3$ and $R^4$ which may be the same or different each represent hydrogen or lower alkyl, Ph represents phenyl, halophenyl, lower alkyl phenyl, di(lower alkyl)phenyl, or lower alkoxy phenyl, R is hydroxy, lower alkoxy or halogen, $R^1$ is phenyl, halophenyl, lower alkyl phenyl, di(lower alkyl)phenyl, lower alkoxy phenyl or naphthyl and $R^6$ is hydrogen or lower alkyl.

Since the compounds of the invention may possess one or more asymmetric carbon atoms, optical enantiomorphs are possible and the compound of the invention may be in the form of the pure enantiomorphs or mixtures of such enantiomorphs, such as racemates.

The term "lower" as used herein means that the radical referred to contains up to 6, preferably up to 4 carbon atoms. It is to be understood that $R^3$ and $R^4$ may be on the same or different carbon atoms, but preferably they are both on the same carbon atom.

In the compounds of formula (I) examples of R groups are hydroxyl, lower alkoxy groups (e.g. methoxy, ethoxy, n-propoxy, n-butoxy) and halo groups such as chloro. Preferably R is hydroxy.

Example of the group $R^1$ are phenyl, halophenyl (for example, fluorophenyl, chlorophenyl or bromophenyl), lower alkyl phenyl or di(lower alkyl)phenyl (where the lower alkyl substituents may be, for example, methyl, ethyl, propyl or butyl), lower alkoxy phenyl (for example, methoxyphenyl, ethoxyphenyl, propoxyphenyl or butoxyphenyl) and naphthyl. Preferably $R^1$ is phenyl or halophenyl such as p-chlorophenyl.

Examples of the group Ph are phenyl, halophenyl, lower alkyl phenyl, di(lower alkyl)phenyl, or lower alkoxyphenyl as mentioned above in connection with the group $R^1$. Preferably Ph is phenyl or halophenyl such as o-, m- or p-chloro or bromophenyl.

When the groups $R^3$ and/or $R^4$ are lower alkyl they can be, for example, methyl, ethyl, propyl or butyl.

The group $R^6$ can be hydrogen or a branched or straight chain lower alkyl group (e.g. methyl, ethyl, propyl or butyl). Preferably $R^6$ is hydrogen.

Compounds of formula (I) in which n is 2 are tetrahydro-1H-1,3-diazepines and compounds in which n is 3 are hexahydro-1,3-diazocines.

Particularly preferred compounds of general formula (I) are:
α-(m-chlorophenyl)-α-phenyl-(4,5,6,7-tetrahydro-1H-1,3-diazepin-2-yl)methanol,
2-(chlorodiphenylmethyl)-4,5,6,7-tetrahydro-1H-1,3-diazepine,
α, α-diphenyl-(4,5,6,7-tetrahydro-1H-1,3-diazepin-2-yl)methanol and
α-(1,4,5,6,7,8-hexahydro-1,3-diazocin-2-yl)-α,α-diphenylmethanol and the pharmaceutically acceptable salts thereof.

The compounds of general formula (I) may be prepared by a process in which a ketone of general formula (II)

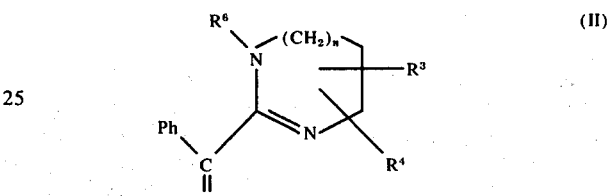

wherein Ph, n, $R^3$, $R^4$ and $R^6$ have the meanings given above, is reacted with an organometallic compound known in the art for the conversion of a ketone function to the

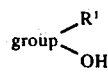

and, if desired a compound in which R represents a hydroxyl group is converted by a replacement reaction to a compound in which R is halo and, if desired the compound in which R is halo is reacted with a lower alkoxide to give a compound in which R is lower alkoxy or a free base of formula (I) is converted into an acid addition salt thereof.

In the above process the organometallic compound is preferably chosen from (a) Grignard reagents of formula $R^1MgY$ wherein Y is halogen and $R^1$ has the meaning defined above, and (b) alkali-metal compounds such as the lithium derivatives of formula $R^1Li$ for example phenyl lithium). The reaction with the organometallic compound is generally carried out in an inert organic solvent, for example ether or tetrahydrofuran, using the standard conditions known for the particular reaction concerned.

As already mentioned, if desired, the compound in which R represents a hydroxyl group may be converted by a replacement reaction into a compound in which R is halo, particularly chloro. For example, the hydroxy compound can be reacted with a hydrohalic acid or an equivalent halogenating agent known for converting alcohols to halides. In a preferred procedure the hydroxy compound is treated with thionyl chloride. The compound in which R is halo, particularly, chloro may be converted into a compound in which R is lower alkoxy by reaction with a lower alkoxide, particularly an alkali metal alkoxide e.g. a sodium alkoxide such as sodium methoxide.

Once a compound of general formula (I) has been prepared any group Ph, R, $R^1$ or $R^6$ may be converted into any other Ph, R, $R^1$ group by known methods. A hydroxyl function R may be etherified to form an alkoxy residue R by the methods described hereinbefore. When $R^6$ is a hydrogen atom the compound can be (lower)alkylated to introduce a lower(alkyl) group $R^6$. If necessary any reactive group in a compound may be protected by known methods before performing any of the above reactions and then removed by known methods subsequent to the reaction.

The starting compounds of general formula (II), may be prepared by oxidation of the corresponding hydroxy compounds of the general formula (III)

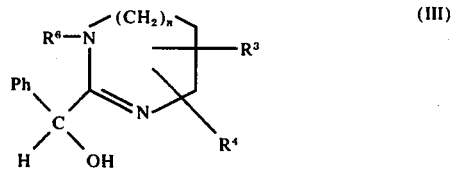

wherein Ph, n, $R^3$, $R^4$ and $R^6$ have the meanings given above. Preferably the oxidation is carried out with a mild oxidising agent such as manganese dioxide (for example in a solvent such as dichloromethane, benzene, acetone or aqueous acetone). It may be desirable to use mild oxidising agents such as precipitated manganese dioxide or precipitated manganese dioxide which has been deactivated (e.g. by stirring with water and then drying).

The compounds of general formula (III) may be prepared by known methods. For example, they may be prepared by the methods described by D. G. Neilson et al., J. Chem. Soc. (C), 1968, 1853 N. W. Bristow, J. Chem. Soc. 1957, 513 or C.H. Tilford et al., J. Amer. Chem. Soc., 1949, 71, 1885.

The compounds of formula (I) are capable of forming acid addition salts with acids, particularly pharmaceutically acceptable acids, and the invention also provides such salts. The salts may be isolated directly from the processes described above or prepared by dissolving the specific compound of formula (I) as its base in a suitable organic solvent, and treating it with a solution of the selected acid, in accordance with conventional procedures for preparing acid addition salts from base compounds generally. As examples of acids, there may be used any of hydrochloric, hydrobromic, tartaric, phosphoric, maleic, citric, acetic or benzoic acid.

The optical isomers of the compounds of formula (I) may be prepared by resolving a racemic mixture by standard methods described in the literature. The racemate may be prepared by any of the processes outlined above. It is to be understood that the resolution may be carried out on the racemic mixture of the final desired product, or it may be carried out on a racemate of one compound of general formula (I) and then optical isomers subjected to afterprocesses to give the desired product of formula (I). The compounds of general formula (I) possess hypoglycaemic activity, as shown by standard tests on warm-blooded animals. The compounds can be tested for hypoglycaemic activity by the following procedure:

Male rats weighing 170–200 grams are fasted overnight. A control blood sample is taken from the tail and the sample of test compound is then administered by stomach tube. Subsequent blood samples are taken at hourly intervals for five hours and the change in the blood sugar concentration is determined. In this procedure it was found that many compounds produced a depression in blood sugar of more than 20% for at least 3 of the hourly test samples when administered at 50 mg/kg or less. Examples of such compounds include: α,α-diphenyl-(4,5,6,7-tetrahydro-1H-1,3-diazepin-2-yl)methanol, α-(m-chlorophenyl)-α-phenyl-(4,5,6,7-tetrahydro-1H-1,3-diazepin-2-yl)methanol and 2-(chlorodiphenylmethyl)-4,5,6,7-tetrahydro-1H-1,3-diazepine.

Many of the compounds possess other pharmacological activity e.g. diuretic, anti-inflammatory and cardiovascular activity. For example many of the compounds show anti-inflammatory properties when tested by the procedures of Winter et al., in Proc. Soc., Biol. Med., 1962, 111, 544 and Buttle et al in Nature, 1957, 179, 629. Some of the compounds have been tested for diuretic activity by the following procedure:

Male rats were fasted for 18 hours (overnight) but had free access to drinking water during this time. Next morning the animals' bladders were emptied by gentle squeezing of the lower abdomen and the compounds were then administered orally as solutions in water. The concentrations of the solutions were adjusted so that each animals received its appropriate dose in a volume equivalent to 25 ml/kg body weight. Pairs of similarly treated animals were placed in metabolism cages (without food or drinking water) and urine was collected for 3 hours. At the end of this period the animals' bladders were emptied as before.

As the compounds of general formula (I) show pharmaceutical activity the invention further provides a pharmaceutical composition which comprises a pharmaceutically active form of a compound provided by the invention in association with a pharmaceutically acceptable carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavoring agents, lubricants, solubilisers, suspending agents, binders, or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by carrier, which is thus in association with it, Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical composition is in unit dosage form. In such form, the composition is subdivided in unit doses containing appropriate quantities of the active ingredient; the unit dosage form can be a packaged composition, the package containing specific quantities of compositions, for example packeted powders or vials or ampoules. The unit dosage form can be a capsule or tablet itself, or it can be the appropriate number of any of these in packaged form. The quantity of active ingredient in a unit dose of composition may be varied or adjusted from 5 mg. or less to 500 mg. or more, according to the particular need and the activity of the active ingredient. The invention also includes the compounds in the absence of carrier where the compounds are in unit dosage form.

The following Examples illustrate the invention.

EXAMPLE 1

α,α-Diphenyl-(4,5,6,7-tetrahydro-1H-1,3-diazepin-2-yl)-methanol

Diaminobutane (17.6g, 0.2 mole) was added to a cooled, stirred solution of ethyl mandelimidate (43.2g 0.2 mole) in absolute ethanol (300 ml). The mixture was stirred for 1 hour allowing to warm up to room temperature and then heated under reflux for 24 hours. The solvent was removed under reduced pressure and the residue dissolved in water and acidified with hydrochloric acid. After extraction with ether the aqueous phase was basified with 10N sodium hydroxide and extracted with chloroform. Combined chloroform extracts were washed with water and dried (MgSO$_4$). After removal of the solvent α-phenyl-(4,5,6,7-tetrahydro-1H-1,3-diazepin-2-yl)-methanol was obtained as colourless needles from isopropanol. (8.7g., m.p. 105°–107°). [Found C, 70.15; H, 8.0; N, 13.4 C$_{12}$H$_{16}$N$_2$O requires C, 70.55; H, 7.4; N, 13.7%].

A solution of α-phenyl-(4,5,6,7-tetrahydro-1H-1,3-diazepin-2-yl)-methanol (10 g.) in dry benzene (500 ml.) was stirred with active manganese dioxide (prepared as described by Attenburrow et al., J. Chem. Soc. 1952, 1094) (120 g.) at room temperature for 24 hours. Filtration and removal of the solvent yielded phenyl (4,5,6,7-tetrahydro-1H-1,3-diazepin-2-yl) ketone as a crude unstable oil (6.31 g.).

A solution of the crude ketone (4.04 g., 0.02 mole) in dry tetrahydrofuran (25 ml.) was added to a stirred solution of phenylmagnesium bromide [made from magnesium (1.2 g., 0.05 mole) and bromobenzene (7.9 g., 0.05 mole)] in dry tetrahydrofuran (ca. 40 ml.) at 0° C. After stirring overnight at room temperature the solution was poured onto ice/ammonium chloride solution, extracted with chloroform, and the combined extracts dried (MgSO$_4$). After removal of the solvent the residue was taken up in benzene, extracted with 2N HCl, the extracts basified and extracted with chloroform. Removal of the solvent from the dried extracts and crystallisation of the crude residue from a small volume of isopropanol yielded the title compound (1.83 g. m.p. 119°–121° C). [Found: C, 77.1; H, 7.2; N, 10.0% C$_{18}$H$_{20}$N$_2$O requires C, 77.1; H, 7.2; N, 10.0% ].

EXAMPLE 2

α-(m-Chlorophenyl)-α-phenyl-(4,5,6,7-tetrahydro-1H-1,3-diazepin-2-yl)methanol

A solution of crude (4,5,6,7-tetrahydro-1H-1,3-diazepin-2-yl)phenyl ketone (4.7 g.) in dry tetrahydrofuran (40 ml.) was added dropwise to a stirred ice-cooled solution of m-chlorophenylmagnesium bromide (0.075 mole) in dry tetrahydrofuran (60 ml.). After the addition the solution was stirred overnight at room temperature and then poured on to ice/ammonium chloride solution, extracted with chloroform and the combined extracts dried. After removal of the solvent the residue was taken up in benzene, extracted with 2N HCl, the extracts basified (NH$_4$OH) and extracted with chloroform. Crystallisation of the crude residue from a small volume of isopropanol yielded white needles (1.595 g.). Recrystallisation from isopropanol gave the pure title compound, m.p. 105°–107° C. [Found: C, 68.6; H, 6.2; N, 9.0%. C$_{18}$H$_{19}$ClN$_2$O requires C, 68.65; H, 6.1; N, 8.9%].

In a similar manner reaction of (4,5,6,7-tetrahydro-1H-1,3-diazepin-2-yl)phenyl ketone with o-methylphenylmagnesium bromide, 2,6-dimethylphenylmagnesium bromide, 4-methoxyphenylmagnesium bromide and 1-naphthylmagnesium bromide gives respectively: α-(o-methylphenyl)-α-phenyl-(4,5,6,7-tetrahydro-1H-1,3-diazepin-2-yl)methanol, α-(2,6-dimethylphenyl)-α-phenyl-(4,5,6,7-tetrahydro-1H-1, 3-diazepin-2-yl)-methanol, α-(4-methoxyphenyl)-α-phenyl-(4,5,6,7-tetrahydro-1H-1,3-diazepin-2-yl)methanol and α-(1-naphthyl)-α-phenyl-(4,5,6,7-tetrahydro-1H-1,3-diazepin-2-yl)methanol.

Similarly reaction of (1-methyl-4,5,6,7-tetrahydro-1H-1,3-diazepin-2-yl)phenyl ketone and (5,5-dimethyl-4,5,6,7-tetrahydro-1H-1,3-diazepin-2-yl)phenyl ketone with phenylmagnesium bromide gives respectively α,α-diphenyl-(1-methyl-4,5,6,7-tetrahydro-1H-1,3-diazepin-2-yl) methanol and α,α-diphenyl-(5,5-dimethyl-4,5,6,7-tetrahydro1H-1,3-diazepin-2-yl)methanol.

EXAMPLE 3

2-(Chlorodiphenylmethyl)-4,5,6,7-tetrahydro-1H-1,3-diazepine hydrochloride

To a stirred solution of α,α-diphenyl-(4,5,6,7-tetrahydro-1H-1,3-diazepin-2-yl)methanol (0.7 g., 0.0025 mole) in dry chloroform (10 ml.) was added thionyl chloride (0.55 ml, 0.0075 mole), the solution stirred one hour at room temperature and then heated under reflux for 3½ hours. After removal of the solvent and excess thionyl chloride under reduced pressure, the residue was crystallised as colourless needles (0.581 g.) from ethanol/ether. Recrystallisation from ethanol/ether gave the title compound (0.481 g.), slow dec. on heating, above ca. 190° C. [Found: C, 64.8; H, 6.1; N, 8.35% C$_{18}$H$_{19}$N$_2$Cl. HCl requires: C, 64.5; H, 6.0; N, 8.35%]

EXAMPLE 4

α-(1,4,5,6,7,8-Hexahydro-1,3-diazocin-2-yl)-α-phenylmethanol

Ethyl mandelimidate hydrochloride (21.6 g., 0.1 mole) was added portionwise to a stirred solution of 1,5-diaminopentane (10.2 g., 0.1 mole) in absolute ethanol (500 ml.) at 0°. After the addition the solution was stirred for 1 hour at 0° and for a further hour at room temperature. The solution was then heated under reflux for 24 hrs. After removal of the solvent the residual oil was dissolved in 1N hydrochloric acid, extracted with ether and then basified with 10N sodium hydroxide solution. The solution was extracted several times with dichloromethane, the combined extracts dried (MgSO$_4$) and the solvent removed to yield a brown oil. Slow crystallisation from a small volume of ethyl methyl ketone yielded the title compound as white crystals (2.17 g., m.p. 142°–146° [slow dec.]). [Found: C, 71.8; H, 8.3; N, 12.8%; C$_{13}$H$_{18}$N$_2$O requires C, 71.5; H, 8.3; N, 12.8%].

The title compound was converted into its hydrochloride salt, m.p. 250°–255° (dec), [Found: C, 61.2; H, 7.5; N, 11.15%; C$_{13}$H$_{18}$N$_2$O.HCl requires C, 61.3; H, 7.5; N, 11.0%].

EXAMPLE 5

(1,4,5,6,7,8-Hexahydro-1,3-diazocin-2-yl)phenyl ketone

A suspension of α-(1,4,5,6,7,8-hexahydro-1,3-diazocin2-yl)-α-phenylmethanol (2.9 g.) in dichloromethane (150 ml.) was stirred with active manganese dioxide (30 g.) for 48 hrs. After filtering through kieselguhr the solvent was removed and the residue crystallised from light petroleum (b.p. 60°–80°) to give the title compound as crude needles (1.4 g.). Recrystallisation from light petroleum gave the pure product, m.p. 70°–71°; [Found: C, 72.3; H, 7.45; N, 12.7%. C$_{13}$H$_{16}$N$_2$O requires: C, 72.2; H, 7.45; N, 12.95%].

EXAMPLE 6

α-(1,4,5,6,7,8-Hexahydro-1,3-diazocin-2-yl)-α,α-diphenylmethanol

A solution of crude (1,4,5,6,7,8-hexahydro-1,3-diazocin-2-yl)phenyl ketone (1.4 g.) in dry tetrahydrofuran (20 ml.) was added dropwise to a stirred solution of phenylmagnesium bromide (0.02 mole) in dry tetrahydrofuran (30 ml.) at 0°. The solution was stirred overnight at room temperature, poured onto ice/ammonium chloride solution, extracted with chloroform and the combined extracts washed and dried (MgSO$_4$). Removal of the solvent and crystallisation of the residue from isopropanol yielded colourless crystals (0.761 g.). The mother liquors were evaporated, the residue dissolved in benzene and extracted with 2N HCl. After basification the solution was worked up as above to give a further 0.302 g. Recrystallisation from isopropanol gave the title compound as a pure product (m.p. 134°–135°). [Found: C, 77.65; H, 7.75; N, 9.35%. C$_{19}$H$_{22}$N$_2$O requires C, 77.5; H, 7.5; N, 9.5%].

In a similar manner reaction of (1,4,5,6,7,8-hexahydro-1,3-diazocin-2-yl)phenyl ketone with m-chlorophenylmagnesium bromide gives α-(m-chlorophenyl)-α)-α-(1,4,5,6,7,8-hexahydro-1,3-diazocin-2-yl)methanol.

EXAMPLE 7

2-(Methoxydiphenylmethyl)-4,5,6,7-tetrahydro-1H-1,3-diazepine 2-(Chlorodiphenylmethyl)-4,5,6,7-tetrahydro-1H-1,3-diazepine hydrochloride (0.003 mole) is stirred at room temperature for two days in dry methanol (25 ml) containing sodium methoxide (0.006 mole). After removal of the solvent the residue is dissolved in chloroform washed with water and dried over magnesium sulphate. Removal of the solvent gives the title compound.

EXAMPLE 8

2-(Chlorodiphenylmethyl)-1,4,5,6,7,8-hexahydro-1,3-diazocine hydrochloride

Thionyl chloride (0.09 mole) is added dropwise to a stirred cooled solution of α-(1,4,5,6,7,8-hexahydro-1,3-diazocin-2-yl)-α,α-diphenylmethanol (0.03 mole) in chloroform (20 ml). The solution is stirred for one hour at room temperature then heated under reflux until evolution of hydrogen chloride ceases. The reaction mixture is cooled and diluted with ether to obtain the title compound.

EXAMPLE 9

2-(Methoxydiphenylmethyl)-1,4,5,6,7,8-hexahydro-1,3-diazocine 2-(Chlorodiphenylmethyl)-1,4,5,6,7,8-hexahydro-1,3-diazocine hydrochloride (0.001 mole) is stirred at room temperature for 2 days in a solution of dry methanol (5 ml) containing sodium methoxide (0.002 mole). After removal of solvent the residue is dissolved in chloroform and washed with water. After drying over magnesium sulphate the solvent is removed to give the title compound.

What is claimed is:

1. A compound selected from the group consisting of bases having the formula

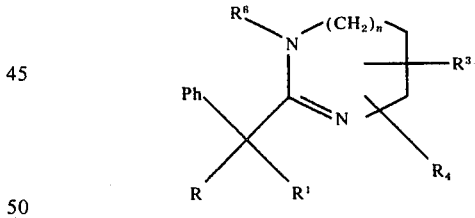

and the pharmaceutically acceptable acid addition salts thereof, wherein n represents 2 or 3, R$^3$ and R$^4$ which may be the same or different each represent a member of the group consisting of hydrogen and alkyl containing from one to six carbon atoms, Ph represents a member of the group consisting of phenyl, halophenyl, alkylphenyl wherein the alkyl radical contains from one to six carbon atoms, dialkylphenyl wherein the alkyl substituents each contain from one to six carbon atoms and alkoxyphenyl wherein the alkoxy substituent contains from one to six carbon atoms, R is a member of the group consisting of hydroxyl, halogen and alkoxy containing from one to six carbon atoms, R$^1$ is a member of the group consisting of phenyl, halophenyl, alkylphenyl wherein the alkyl substituent contains from one to six carbon atoms, dialkylphenyl wherein the alkyl substitutents each contain from one to six carbon atoms, alkoxyphenyl wherein the alkoxy substituent contains from one to six carbon atoms and naphthyl, and $R^6$ is a member of group consisting of hydrogen and alkyl containing from one to six carbon atoms.

2. A compound according to claim 1 which is α,α-diphenyl-(4,5,6,7-tetrahydro-1H-1,3-diazepin-2-yl)methanol.

3. A compound according to claim 1 which is α-(m-chlorophenyl)-α-phenyl-(4,5,6,7-tetrahydro-1H-1,3-diazepin-2-yl)methanol.

4. A compound according to claim 1 which is 2-(chlorodiphenylmethyl)-4,5,6,7-tetrahydro-1H-1,3-diazepine.

5. A compound according to claim 1 which is α-(1,4,5,6,7,8-hexahydro-1,3-diazocin-2-yl)-α,α-diphenylmethanol.

* * * * *